USOO5851535A

United States Patent [19]
Jolivet-Reynaud

[11] Patent Number: 5,851,535
[45] Date of Patent: Dec. 22, 1998

[54] **MIMOTOPIC POLYPEPTIDES OF *TOXOPLASMA GONDII* AND APPLICATIONS**

[75] Inventor: Colette Jolivet-Reynaud, Bron, France

[73] Assignee: Bio Merieux, Marcy L'Etoile, France

[21] Appl. No.: 592,646

[22] Filed: Jan. 26, 1996

[30] Foreign Application Priority Data

Jan. 30, 1995 [FR] France .................................. 95 01297

[51] Int. Cl.$^6$ ................................................. A61K 39/012
[52] U.S. Cl. ..................................... 424/273.1; 424/184.1; 424/191.1; 530/350; 530/387.1; 530/387.2; 530/388.1; 530/388.6; 530/324; 530/330
[58] Field of Search ................................ 530/350, 387.1, 530/387.2, 388.1, 324–330, 388.6; 424/184.1, 191.1, 273.1

[56] References Cited

FOREIGN PATENT DOCUMENTS

| 8908700 | 9/1989 | WIPO . |
| WO 89/12683 | 12/1989 | WIPO . |
| WO 94/17813 | 8/1994 | WIPO . |
| 9602654 | 2/1996 | WIPO . |

OTHER PUBLICATIONS

Isabelle Godard et al., "Antigenicity and Immunogenicity of P30–Derived Peptides in Experimental Models of Toxoplasmosis", *Molecular Immunology*, vol. 31, No. 17, pp. 1353–1363, 1994.

Brian G. Grimwood et al., "*Toxoplasm Gondii*: Purification of Trophozoites Propagated in Cell Culture", *Experimental Parasitology*, vol. 48, pp. 282–286, 1979.

Jamie K. Scott et al., "Searching for Peptide Ligands with an Epitope Library", *Science*, vol. 249, pp. 386–390, Jul. 1990.

J. Lawrence Burg et al, "Molecular Analysis of the Gene Encoding the Major Surface Antigen of *Toxoplasma gondii*", *The Journal of Immunology*, vol. 141, No. 10, pp. 3584–3591, Nov. 15, 1988.

H. Mario Geysen et al., "Strategies for Epitope Analysis Using Peptide Synthesis", *Journal of Immunological Methods*, vol. 102, pp. 259–274, 1987.

Lloyd H. Kasper et al., "Purification of a Major Membrane Protein of *Toxoplasma Gondii* by Immunoabsorption with a Monoclonal Antibody", *The Journal of Immunology*, vol. 130, No. 5, pp. 2407–2412, May 1983.

Benjamin J. Luft et al., "Toxoplasmic Encephalitis in Patients With Acquired Immune Deficiency Syndrome", *JAMA*, vol. 252, No. 7, pp. 913–917, Aug. 17, 1984.

H.P.A. Hughes, "Toxoplasmosis: The Need for Improved Diagnostic Techniques and Accurate Risk Assessment", *Current Topics in Microbiology and Immunology*, vol. 120, pp. 105–139, 1985.

Arthur E. Farkash et al., "CNS toxoplasmosis in Acquired Imune Deficiency Syndrome: A Clinical–Pathological–Radiological Review of 12 Cases", *Journal of Neurology, Neurosurgery, and Pyschiatry*, vol. 49, pp. 744–748, 1986.

Rolf H. Berg et al., "Long–Chain Polystyrene–Grafted Polyethylene Film Matrix: A New Support for Solid–Phase Peptide Synthesis", *J. Am. Chem. Soc.*, vol. 111, pp. 8024–8026, 1989.

*Primary Examiner*—James C. Housel
*Assistant Examiner*—Jennifer Shaver
*Attorney, Agent, or Firm*—Oliff & Berridge, PLC

[57] ABSTRACT

The invention relates to a polypeptide capable of reacting specifically with an anti-*Toxoplasma gondii* P30 protein antibody, and comprising a peptide sequence, in which any succession of 6 contiguous amino acids exhibits at most 67% homology with the peptide sequence of said P30 protein, identified by SEQ ID No.1, or comprising a sequence derived from said peptide sequence, and the applications of this polypeptide especially for detecting a *Toxoplasma gondii* infection, in a biological sample.

16 Claims, 3 Drawing Sheets

MIMOTOPIC POLYPEPTIDES OF *TOXOPLASMA GONDII* AND APPLICATIONS

The present invention relates to a polypeptide, capable of being substituted for a *Toxoplasma gondii* antigen, a polynucleotide whose expression corresponds to said polypeptide, and their use for diagnostic and therapeutic purposes.

BACKGROUND OF THE INVENTION

Toxoplasmosis is an infectious disease caused by a *Toxoplasma gondii* protozoal parasite, a member of the class Sporozoa, and of the order Coccidia. *Toxoplasma gondii* is an intracellular parasite which reproduces in a wide variety of cell types in its hosts, which are mammals.

This parasite, which is very widespread geographically, is an important pathogenic agent, not only in human medicine, but also in veterinary medicine.

In man, two forms of the parasite have been described: the "tachyzoite", which is the multiplicative form encountered during the acute phase of the disease and the "bradyzoite", a resistant form which persists encysted in the nervous tissues, and which is probably responsible for maintaining a durable immunity to reinfection.

In humans, toxoplasmosis is most often asymptomatic and most often passes unnoticed without any consequences. There are however cases for which a Toxoplasma infection or a reactivation of a previously acquired infection can generate serious disorders for the so-called at risk individuals who are pregnant women and immunodepressed and immunosuppressed subjects. This organism has multiple replication sites. Thus, it may be responsible for severe cerebral and ocular impairments when its replication site is the cells of the central nervous system and the cells of the reticuloendothelial system. Pregnant women represent high-risk subjects, since a Toxoplasma infection, especially during the first few months of pregnancy, may be responsible for serious fetal and neonatal complications if maternal treatment is not undertaken early and pursued assiduously. In particular, newborns contaminated via the transplacental route are subject to serious ocular and cerebral disorders which are even fatal in certain cases. Immunodepressed patients and particularly AIDS patients are subject to serious Toxoplasmosis due most often to reactivations of previous infections, although dissemination following a primary infection cannot be completely excluded (see FARKASH et al., J. Neurology, Neurosurgery and Psychiatry 1986, 49, 744–748 and Luft et al., J. Am. Med. Ass. 1984, 252, 913–917).

It is therefore essential to have available diagnostic tests which make it possible to determine the presence of the parasite, especially in pregnant women, either by detecting specific antibodies or by detecting Toxoplasma antigens in the subject.

DESCRIPTION OF THE PRIOR ART

HUGUES in "Current topics in Microbiology and Immunology" (Vol. 120, 1985, SPRINGER Ed., pages 105–139) has listed a number of commercially available serodiagnostic tests such as the SABIN and FELDMAN staining test, standardized by BEVERLY and BEATTLE in 1958 and perfected by FELDMAN and LAMB (1966), WALDELAND (1976) and BALFOUR et al. (1982); the REMINGTON (1968) test for the detection of antibodies by immunofluorescence, optimized in 1975 by KARIM and LUDLAM; the hemagglutination tests; the ELISA test for the detection of antibodies specific for Toxoplasma, by the isolation of IgM in situ on a microplate described in 1983 by WIELARRD et al.

The different tests used are based on the formation of immune complexes between the *Toxoplasma gondii* antigens and their specific antibodies. One of the critical points therefore consists in the characterization of the *Toxoplasma gondii* major antigens, which induce a specific immune response and are capable of being used in serological detection tests.

Some authors have shown that most of the monoclonal antibodies directed against the *Toxoplasma gondii* surface recognize a protein of 27 to 35 KDa, called P30 (Kasper et al.; 1983, J. Immunol. 130, 2407–2412). Several studies have demonstrated that this P30 protein is a major surface antigen which can be used for the production of vaccines or in diagnostic tests, especially in immunoassays. Moreover, Boothroyd et al. (see Patent Application WO 89/08700) have identified and obtained the genetic material encoding the *Toxoplasma gondii* P30 protein and suggested the use of the gene for the production of recombinant protein, peptides and antibodies. This gene has been cloned (Burg et al., 1988, J. Immunol., 141, 3584–3591). Analysis of the sequence shows a potential N-glycosylation site, a secretory signal positioned at the N-terminal end which is cleaved in the mature P30 protein and a highly hydrophobic C-terminal region which is also cleaved and replaced by a glycolipid which allows membrane anchorage of the P30 protein.

There remains, however, a problem which consists in producing sufficient quantities of the P30 antigen. Indeed, three approaches are currently available, with the aim of obtaining antigens and parts of P30 antigens which can be used especially in diagnostic procedures.

The first consists in performing cultures of the *Toxoplasma gondii* parasite in a large number of infected mice, in collecting the natural *Toxoplasma gondii* antigens, and especially P30, via the peritoneal route and in purifying them. However, this technique has many disadvantages such as the cost, the need of having available experienced staff and a large number of animals, the complexity of the technique or the difficulties linked with the extraction which is not very efficient.

The second approach, derived from the preceding one, involves the in vitro culture of the parasite in cell cultures (Grimwood et al. 1979, Experimental Parasitology, 48, 282–286). However, this approach does not make it possible to overcome the disadvantages of cost or extraction mentioned above.

The third approach refers to genetic recombination technologies and consists in introducing and cloning into a prokaryotic, eukaryotic or viral genome all or part of the gene encoding the P30 protein, in expressing said gene in a host cell and in extracting the recombinant P30 protein obtained. This technique offers many advantages but suffers from a low level of expression of the protein. Moreover, Burg et al. (1988, Journal of Immunology, 141, 3584–3591) has shown that the natural P30 protein is a highly structured antigen exhibiting conformational constraints. The conformation of the P30 protein is a critical element for its recognition by specific antibodies and results especially from the presence of disulphide bridges in the protein. Now, it is difficult, through genetic recombination, to perfectly control the post-translational modifications to which the synthesized proteins are subjected. Consequently, it is difficult to obtain, by genetic recombination, a P30 protein or a part of said protein which is appropriately matured so that it adopts a conformation which is sufficiently close to that of the natural P30 protein to allow specific recognition by antibodies directed against said protein.

In accordance with the document WO-A-89/12683, polypeptides are described which are capable of reacting with an anti-*Toxoplasma gondii* P30 protein antibody and which possess a peptide sequence chosen from the sequence SEQ ID No.15, fragments of SEQ ID No.15, SEQ ID No.16, SEQ ID No.17 and SEQ ID No.18, which are identified at the end of the description. These polypeptides were determined from the peptide sequence of a *Toxoplasma gondii* protein, and consist of the sequence of the latter or of the antigenic fragments of the latter. Given the low level of homology of said sequences with that of the P30 protein, it can be stated that the peptide sequence of the protein at the origin of these polypeptides is not that of the P30 protein. These polypeptides pose the problem of their specificity; indeed, they have antigenic properties toward anti-P30 antibodies, but they probably have the same properties toward antibodies directed against the protein from which they were defined.

Surprisingly, it has been shown that a polypeptide synthesized by the chemical route or by genetic recombination methods, which has been subjected to no modification after its synthesis, is capable of being recognized by antibodies specific for the P30 protein, designated anti-P30 antibodies.

Before embarking on the subjects of the invention, various terms used in the description which will follow are defined below.

"Protein P30" is understood to mean the *Toxoplasma gondii* major antigen, therefore the peptide sequence is identified by the reference SEQ ID No.1.

"Sera from individuals or animals infected by *Toxoplasma gondii*" is understood to mean especially sera from patients who have contracted a recent or previous *Toxoplasma gondii* infection and who contain immunoglobulins recognizing specifically all or part of the P30 protein.

Of course, a polypeptide according to the invention may also be recognized by other antibodies, such as for example monoclonal or polyclonal antibodies obtained by immunizing a variety of species with the natural P30 protein, the recombinant P30 protein or fragments or peptides thereof.

"Polypeptide" designates a peptide or a peptide fragment, or a protein, obtained by chemical synthesis or by genetic recombination techniques. The polypeptides according to the invention can be obtained by conventional methods of synthesis, for example in an automated peptide synthesizer, or by genetic engineering techniques comprising the insertion of a DNA sequence encoding said polypeptide into an expression vector such as a plasmid or a virus as described in the present application, and the transformation of cells with this expression vector and the culture of these eukaryotic or prokaryotic cells.

The degree of homology of a first peptide sequence, compared with a second reference peptide sequence, characterizes the maximum degree, expressed as a percentage, of identity between the two sequences. It is evaluated, for a succession of a given number of contiguous amino acids, by the alignment of the two sequences, and by displacing one relative to the other, and by comparing the amino acids in the two sequences.

"Sequence derived from another amino acid sequence" is understood to mean an amino acid sequence modified by insertion and/or deletion and/or substitution and/or extension and/or shortening and/or chemical modification of one or more amino acids, excluding any peptide sequence in which any succession of 20 contiguous amino acids exhibits at least 40% homology with the peptide sequence of the P30 protein (SEQ ID No.1), so long as these modifications preserve substantially or even enhance the properties of said sequence. Thus, "derived sequence" is understood to mean especially the sequences in which one or more amino acid(s) is (are) substituted by one or several other amino acid(s) as illustrated in Example 6; the sequences in which one or more amino acid(s) of the L series is (are) replaced by an amino acid of the D series, and vice versa; the sequences into which there has been introduced a modification of the side chains of the amino acids, such as for example an acetylation of the amine functional groups, a carboxylation of the thiol functional groups, an esterification of the carboxylic functional groups; a modification of the peptide bonds such as, for example, of the carba, retro, inverso, retro-inverso, reduced and methyleneoxy bonds.

"Polynucleotide" is understood to mean either a DNA sequence, or an RNA sequence, or a cDNA sequence resulting from the reverse transcription of an RNA sequence, of natural or synthetic origin, with or without modified bases.

SUMMARY OF THE INVENTION

The subject of the present invention is a polypeptide capable of reacting specifically with an anti-*Toxoplasma gondii* P30 protein antibody, and comprising a peptide sequence, having, in any succession of 6 contiguous amino acids, at most 67% homology with the peptide sequence of said P30 protein, as identified by SEQ ID No.1, or comprising a sequence derived from said peptide sequence.

Preferably, a polypeptide of the invention comprises a peptide sequence, having, in any succession of 11 contiguous amino acids, at most 36% homology with said peptide sequence SEQ ID No.1, or comprises a derived sequence. A specific polypeptide of the invention possesses a peptide sequence consisting of a peptide sequence, having, in any succession of 11 contiguous amino acids, at most 36% homology with said peptide sequence SEQ ID No.1, or consisting of a derived sequence.

The subject of the present invention is also a polypeptide capable of reacting specifically with an anti-*Toxoplasma gondii* P30 protein antibody, which possesses a peptide sequence comprising SEQ ID No.2, or a derived sequence.

The peptide sequence of such a polypeptide advantageously comprises a sequence chosen from SEQ ID No.3, SEQ ID No.4, and their respective derived sequences.

In particular, said peptide sequence comprises a sequence chosen from SEQ ID No.5, SEQ ID No.6, and their respective derived sequences.

Still more preferably, said peptide sequence comprises a sequence chosen from SEQ ID No.7, SEQ ID No.8, SEQ ID No.9, SEQ ID No.10, and their respective derived sequences.

A specific polypeptide of the invention possesses a peptide sequence consisting of a sequence chosen from SEQ ID No.2, SEQ ID No. 3, SEQ ID No.4, SEQ ID No.5, SEQ ID No.6, SEQ ID No.7, SEQ ID No.8, SEQ ID No.9, SEQ ID No.10, and their respective derived sequences.

The polypeptide as defined above may be of phage or viral or bacterial or lower eukaryotic or higher eukaryotic origin.

In particular, this polypeptide may be an envelope peptide fragment, a membrane peptide fragment or a peptide fragment capable of being excreted.

Moreover, said polypeptides may be conjugated, according to techniques well known to persons skilled in the art, to a carrier molecule such as for example a natural or recombinant protein (with the exception of the natural or recombinant P30 protein), a synthetic polymer of amino acids or of aliphatic chains, a nucleic fragment or to a tracer molecule such as for example an oligo-nucleotide, an enzyme such as especially horseradish peroxidase, alkaline phosphatase or galactosidase, or alternatively a radioelement or attached to any support.

It is clearly understood that any peptide sequence different from those described in the invention, and likely to be contained in the peptide sequence of a polypeptide of the invention should not, as such, be capable of reacting with an anti-P30 protein antibody.

A second subject of the present invention is an application of a polypeptide as described above and consists of a reagent for the detection of a *Toxoplasma gondii* infection, said reagent comprising, as reactive substance, a polypeptide of the invention.

A third subject of the invention is a kit for the detection of a *Toxoplasma gondii* infection, comprising the reagent described above, supported by a solid support, immunologically compatible with said reagent.

The term solid support as used here is, without limitation, in the form of a microtiter plate, a sheet, a cone, a well, a bead, or any other appropriate micro-particulate substrate, and includes all materials on which peptide fragments of the invention can be immobilized. This may be synthetic materials which are chemically modified or otherwise, especially polysaccharides, such as cellulose materials, for example paper, cellulose derivatives such as nitrocellulose and cellulose acetate; polymers such as vinyl chloride, polyethylene, polystyrene, polyacrylate, or copolymers such as propylene and vinyl chloride polymer, vinyl chloride and vinyl acetate polymer; styrene-based copolymers; natural fibers such as cotton and synthetic fibers such as nylon. Preferably, the solid support is a polystyrene polymer, a butadiene/styrene copolymer or a butadiene/styrene copolymer mixed with one or more polymers or copolymers chosen from polystyrene, styrene/acrylonitrile or styrene/methyl methacrylate copolymers, polypropylenes, polycarbonates and the like.

The attachment of the reagent to the solid support may be performed in a direct or indirect manner.

In a direct manner, two approaches are possible: either by adsorption of the reagent onto the solid support, that is to say via non-covalent bonds (mainly of the hydrogen, Van der Waals or ionic type), or by establishment of covalent bonds between the reagent and the support. In an indirect manner, an "anti-reagent" compound capable of interacting with the reagent can be attached beforehand (by adsorption or covalent bonding) onto the solid support so as to immobilize the whole on the solid support.

The invention provides, in addition, a process for the detection and/or separation, and especially purification, and/ or assay of anti-P30 protein antibodies in a sample of biological fluid comprising the following steps: a said sample is brought into contact with the reagent of the invention, under conditions which allow an immunological reaction, and then the immune complex which may be formed is detected, separated and/or quantified.

According to a variant, the invention provides a process for assaying the *Toxoplasma gondii* P30 protein in a sample of a biological fluid, which is carried out by a competition technique, during which said sample is brought into contact simultaneously with a predetermined quantity of anti-P30 protein antibodies, and a predetermined quantity of a reagent of the invention, and the quantity of P30 protein in said sample is determined by deduction from the measured quantity of the complex formed between the reagent and said anti-P30 protein antibodies.

According to another variant of a process of the invention for assaying the P30 protein in a sample of a biological fluid, in a first instance, said sample is brought into contact with a predetermined quantity of anti-P30 protein antibodies, in a second instance, a predetermined quantity of a reagent of the invention is added and the quantity of P30 protein in said sample is determined by deduction from the measured quantity of the complex formed between the reagent and said anti-P30 protein antibodies.

These processes may be based on a radioimmunological method of the RIA, RIPA or IRMA type or an immunoenzymatic method of the Western-blot or ELISA type.

Another application of the polypeptide of the invention is an active immunotherapeutic composition, especially a vaccinal preparation, comprising, as active ingredient, a polypeptide described above, said active ingredient being optionally conjugated with an immunologically appropriate support, and optionally a pharmaceutically acceptable excipient.

The invention provides, in addition, a polynucleotide encoding a polypeptide described above. This polynucleotide comprises a nucleotide sequence especially chosen from SEQ ID No.11, SEQ ID No.12, SEQ ID No.13, SEQ ID No.14.

It also relates to a functional expression cassette allowing the expression of a polynucleotide of the invention and comprising the latter, as well as a vector and a eukaryotic or prokaryotic cellular system comprising an expression cassette.

DESCRIPTION OF THE DRAWINGS

The present invention is now illustrated using the examples 1 to 7 and the drawings in which.

Figure 1:
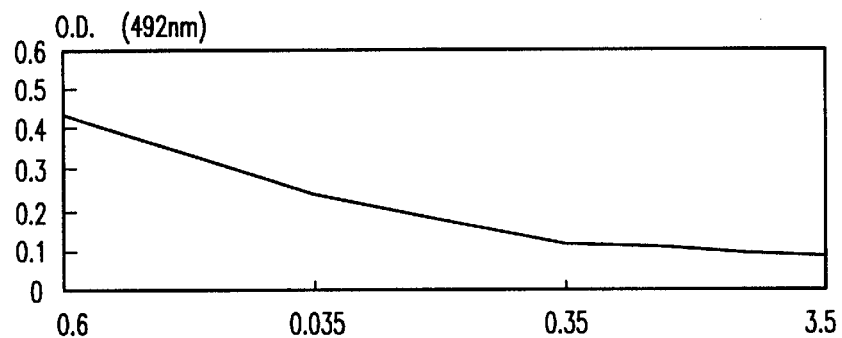
FIG. 1 illustrates the inhibition, by the native P30 protein, of the ELISA response obtained with the phage clone identified in Example 2. The concentrations, expressed in µg/ml, of the P30 protein preincubated with 6 nM anti-P30 monoclonal antibody are indicated on the x-axis and the optical density values measured at 492 nm on the y-axis.

(7) DGAWHWRHRIPLQLA (SEQ ID NO.25) (18) LQLAAGRGAAGAETV (SEQ ID NO.35)
(8) GAWHWRHRIPLQLAA (SEQ ID NO.26) (19) QLAAGRGAAGAETVE (SEQ ID NO.36)
(9) AWHWRHRIPLQLAAG (SEQ ID NO.27) (20) LAAGRGAAGAETVES (SEQ ID NO.37)
(10) WHWRHRIPLQLAAGR (SEQ ID NO.28) (21) AAGRGAAGAETVESC (SEQ ID NO.38)
(11) HWRHRIPLQLAAGRG (SEQ ID NO.29) (22) AGRGAAGAETVESCL (SEQ ID NO.39)

FIGS. 4A to 4F represent the ELISA responses of various substitution mutants of the peptide His-Arg-Ile-Pro-Leu-Gln-Leu-Ala-Ala-Gly-Arg-Gly-Ala-Ala-Gly (SEQ ID NO.9) which are as follows:

A: substitution of the histidine in position 1 X-Arg-Ile-Pro-Leu-Gln-Leu-Ala-Ala-Gly-Arg-Gly-Ala-Ala-Gly (SEQ ID NO.40)

B: substitution of the arginine in position 2 His-X-Ile-Pro-Leu-Gln-Leu-Ala-Ala-Gly-Arg-Gly-Ala-Ala-Gly (SEQ ID NO.41)

C: substitution of the proline in position 4 His-Arg-Ile-X-Leu-Gln-Leu-Ala-Ala-Gly-Arg-Gly-Ala-Ala-Gly (SEQ ID NO.42)

D: substitution of the isoleucine in position 3 His-Arg-X-Pro-Leu-Gln-Leu-Ala-Ala-Gly-Arg-Gly-Ala-Ala-Gly (SEQ ID NO.43)

E: substitution of the leucine in position 7 His-Arg-Ile-Pro-Leu-Gln-X-Ala-Ala-Gly-Arg-Gly-Ala-Ala-Gly (SEQ ID NO.44)

F: substitution of the glutamine in position 6 His-Arg-Ile-Pro-Leu-X-Leu-Ala-Ala-Gly-Arg-Gly-Ala-Ala-Gly (SEQ ID NO.45)

The star designates the response obtained with the wild-type peptide.

The amino acids are represented on the x-axis according to their one-letter nomenclature, the optical density values measured at 405 nm are indicated on the y-axis.

DESCRIPTION OF THE PREFERRED EMBODIMENTS

The invention will be understood more clearly with the aid of the following examples. It should be clearly understood, however, that these examples are given solely by way of illustrating the subject of the invention, and do not in any manner constitute a limitation thereof.

EXAMPLE 1

Selection of a pentadecapeptide capable of reacting specifically with an anti-P30 monoclonal anti-body.

In a first instance, a pentadecapeptide expression library was constructed in a filamentous phage according to the method described by Scott and Smith (1990, Science, 249, 386–390). This library was produced by inserting a synthetic oligonucleotide into a gene encoding a phage envelope protein (protein PIII) of which five copies are present at the surface of the phage. This oligonucleotide consists of a sequence having a degenerate code [(NNK)$^{15}$] where NNK represents a mixture equal to codons corresponding to the 20 amino acids and the Amber stop codon. This expression library makes it possible to obtain, at the surface of the phage, five copies of a fused protein (PIII-pentadecapeptide). The site of insertion of the pentadecapeptide into the sequence of the PIII protein corresponds to the sequence: $NH_2$-Ala-Asp-Gly-Ala-[pentadecapeptide]-Gly-Ala-Ala-Gly-Ala-Glu-Thr-Val-Glu-COOH (SEQ ID NO.46).

In a second instance, the bottom of the Petri dishes 35 mm in diameter is treated with 1 ml of a streptavidin solution at the concentration of 10 µg/ml in 0.1M $NaHCO_3$ and incubated overnight at 4° C. After removal of the streptavidin solution, a solution of 0.1M $NaHCO_3$, 0.1% bovine serum albumin (BSA), 0.1 µg/ml of streptavidin and 0.02% $NaN_3$ is added in order to saturate the non-specific binding sites and the whole is incubated for 2 hours at room temperature. The Petri dishes are washed 6 times with TBS buffer (0.1M Tris buffer, pH 7.2)/0.5% Tween and 10 µg of biotinylated anti-P30 monoclonal antibody 1E1E7 (BioMé rieux) are then incubated overnight at 4° C. in the Petri dishes treated as described above. This makes it possible to obtain, in a known manner, Petri dishes at the bottom of which are immobilized said antibodies via streptavidin.

A sample of the expression library containing about $10^{12}$ virions is then incubated for four hours at 4° C. in the presence of said biotinylated antibodies attached to the bottom of the Petri dish. After several washes with TBS, the phages which have remained attached to the anti-P30 antibodies are eluted with 400 µl of a 0.1N HCl solution, pH 2.2, containing 0.1% BSA, and then neutralized with 75 µl of a 1M Tris-HCl solution, pH 9.1

After concentrating to 100 µl, the suspension of eluted phages is subjected to an amplification step by infecting a suspension at 5 $10^9$ bacteria/ml of a strain of E. coli (K91Kan). The infected bacteria (see Sambrook et al., 1989. Molecular Cloning: A Laboratory Manual, 2nd Edition, Cold Spring Harbor Laboratory, Cold Spring Harbor) are incubated for 45 minutes at 37° C. in 20 ml of NZY medium (tryptone 10 g/l, yeast extract 5 g/l, NaCl 5 g/l, pH adjusted to 7) containing 0.2 µg/ml of tetracycline. The tetracycline concentration of the medium is then raised to 20 mg/ml. With the infectious phages carrying a tetracycline-resistance gene, only the bacteria which were infected by the phage are amplified. The bacterial culture is continued overnight at 37° C. After centrifugation of the culture in order to remove the bacterial cells, 3 ml of polyethylene glycol (PEG) 16.3%-NaCl 3.3M are added to the supernatant in order to precipitate the phages present. After an overnight incubation at 4° C. and centrifugation, the phage pellet is taken up in 1 ml of TBS (0.1M Tris buffer, pH 7.2) and reprecipitated with 150 µl of PEG/NaCl. Centrifugation makes it possible to obtain a phage pellet which is resuspended in 200 µl of TBS. The phage concentration after this amplification is about 2 $10^{13}$ virions/ml.

About $10^{12}$ virions derived from the preceding amplification step are incubated with a 100 nM solution of monoclonal antibody 1E1E7, overnight at 4° C. This mixture is then placed in a Petri dish previously treated with streptavidin and incubated for ten minutes at room temperature. The Petri dish is washed several times with TBS (0.1M Tris buffer, pH 7.2)/Tween 0.5% and the phages which remained attached to the anti-P30 monoclonal antibodies are eluted as described above.

After another phage amplification phase using 100 µl of eluted phages and another phase of selection by anti-P30 monoclonal antibodies 1E1E7 (at the concentration of 0.1 nM), 58 infected bacterial colonies are isolated and 30 chosen at random are inoculated individually into 1.7 ml of NZY-tetracycline medium (20 µg/ml). After a 16 to 24 hour shake culture at 37° C., the cells are removed by centrifugation. The supernatant (1 ml) is mixed with 150 µl of a PEG/NaCl solution and incubated for four hours at 4° C. After centrifugation, the phages are resuspended in 500 µl of TBS.

The phage preparations thus obtained contain about 5 $10^{11}$ phages per millilitre.

This phage selection from an expression library was performed with a monoclonal antibody specific for the P30 protein. Moreover, it was checked that the phages, in which no oligonucleotide was inserted, do not react with this same antibody. Consequently, the nucleic sequence introduced into the selected phage clones should correspond to a pentadecapeptide which allows the recognition of the phage by the anti-P30 antibodies 1E1E7.

EXAMPLE 2

Determination of the sequence of the phage clones selected and immunological analysis of said clones by the ELISA technique.

The DNA of phages corresponding to the 30 clones chosen was prepared according to the method described by Sambrook et al., 1989. Molecular Cloning: A Laboratory Manual, 2nd Edition, Cold Spring Harbor Laboratory, Cold Spring Harbor.

The sequencing of these clones was carried out according to the manufacturer's procedure (United States Biochemicals) with the Sequenase enzyme (trade name) using a primer of 18 bases (5-TGAATTTTCTGTATGAGG-3) (SEQ ID NO.47). This primer is complementary to nucleotides 1663–1680 of the gene encoding the native PIII protein of the phage.

The nucleic sequences obtained, when they are converted into amino acid sequences, indicate that the peptide sequence Trp-His-Trp-Arg-His-Arg-Ile-Pro-Leu-Gln-Leu-Ala-Ala-Gly-Arg (SEQ ID NO.48) is found a large number of times in the clones selected. Indeed, as shown in the following table, of the 30 clones sequenced, eleven of them correspond to this sequence.

| Sequence of the phage clones | Number of identical sequences |
|---|---|
| WHWRHRIPLQLAAGR(SEQ ID NO. 48) | 11 |
| RHWRHRKPLQLATGR(SEQ ID NO. 49) | 1 |
| LAFHRFNLSRPLQRD(SEQ ID NO. 50) | 4 |
| THSHQWRHHQFPAPT(SEQ ID NO. 51) | 3 |
| RRWVRYPVHLHSPIV(SEQ ID NO. 52) | 5 |
| ARFPKELRGSVRSAH(SEQ ID NO. 53) | 1 |
| GSWVLRHSSVGFHFV(SEQ ID NO. 54) | 1 |
| GSFHWFRGSRHVVVH(SEQ ID NO. 55) | 1 |
| SWRFFHSGMPRVSRS(SEQ ID NO. 56) | 1 |
| GSPHRYRGARHVAVD(SEQ ID NO. 57) | 1 |
| WKALFSHSYRSSGVP(SEQ ID NO. 58) | 1 |

The importance of this motif was then analyzed by an immunoenzymatic test, by carrying out an ELISA test for each of the 30 phage clones selected. However, it should be noted that after the purification step, the clones to be tested do not all have the same phage concentration and that these differences can cause aspecific variations of the Optical Density measurements during the ELISA test. In order to overcome this problem, the attachment of the phages onto the ELISA plates was standardized by the use of anti-M13 phage antibodies added to a fixed saturating concentration.

Thus, in a first instance, 100 μl of anti-M13 phage antibodies diluted 1/1000 in 0.1M NaHCO$_3$, pH 8.6 (marketed by Prinn, Inc. Boulder, Colo. 80303), are attached overnight in the wells of Nunc maxisorb (tradename) microtiter plates. After two washes with TBS/Tween 0.05%, 100 μl of the various purified phage clones are then incubated for two hours at 37° C. in the wells. The saturation of the aspecific sites is carried out with TBS containing 1% BSA for two hours at 37° C. After three washes with TBS/Tween 0.05%, 100 μl of the anti-P30 monoclonal antibody 1E1E7, at the concentration of 3 nM, 4 nM or 6 nM, are added and incubated overnight at 4° C. After four washes with TBS/Tween 0.05%, 100 μl of anti-mouse conjugate labeled with peroxidase (marketed by Jackson Immuno Research Laboratories Inc.) are added before incubating for one hour at 37° C. The enzymatic reaction for visualization is carried out by adding 100 μl of an H$_2$O$_2$/ortho-phenylenediamine (OPD) solution and incubating the sample for 30 minutes at room temperature. The staining reaction is stopped by adding 50 μl of 1.8N sulfuric acid. The optical density is measured on a BioMérieux plate reader at 492 nm.

These results, obtained by ELISA, confirm the previous sequencing results because the phage clones for which the best ELISA responses are observed (OD varying between 0.269 and 0.274 for a concentration of monoclonal antibody 1E1E7 of 3 nM) possess a nucleic sequence corresponding to the pentadecapeptide Trp-His-Trp-Arg-His-Arg-Ile-Pro-Leu-Gln-Leu-Ala-Ala-Gly-Arg (SEQ ID NO.48). The sequence of the clones for which a negative response is observed does not exhibit any homology with this sequence. In addition, the results show that the higher the concentration of monoclonal antibody 1E1E7 present in the test, the higher the immunoenzymatic response.

EXAMPLE 3

Inhibition, by the native P30 protein, of the ELISA response obtained with the phage clone identified.

A competition ELISA test was carried out in order to determine if the response obtained with the phage clone identified is inhibited by pre-incubation of the anti-P30 monoclonal antibody 1E1E7 with the P30 protein.

The ELISA test is carried out as described in Example 2 with the following modifications: the monoclonal antibody 1E1E7 (at the concentration of 6 nM) is preincubated with various concentrations of P30 protein for 20 minutes at 37° C. and then the mixture is added to the wells of the ELISA plate in which the phages corresponding to the pentadecapeptide Trp-His-Trp-Arg-His-Arg-Ile-Pro-Leu-Gln-Leu-Ala-Ala-Gly-Arg (SEQ ID NO.48) are attached.

The results obtained show that the ELISA response is inhibited by 45% for a P30 protein concentration of 35 ng/ml. This inhibition is up to 80% with a P30 protein concentration of 3.5 μg/ml.

The results obtained (FIG. 1) are standardized by using anti-M13 antibodies as described above. The decrease in the immunoenzymatic response observed clearly demonstrates that the phage clone identified is recognized by the same antibodies capable of recognizing the P30 protein. The phage clone identified, and especially the pentadecapeptide Trp-His-Trp-Arg-His-Arg-Ile-Pro-Leu-Gln-Leu-Ala-Ala-Gly-Arg (SEQ ID NO.48), is therefore a competitor for the native P30 protein, which is capable of becoming substituted for said P30 protein.

EXAMPLE 4

Specificity of the anti-*Toxoplasma gondii* human antibodies for the sequence Trp-His-Trp-Ara-His-Arg-Ile-Pro-Leu-Gln-Leu-Ala-Ala-Gly-Arg (SEQ ID NO.48) carried by the phage clone identified.

The monoclonal antibody 1E1E7 recognizes an immunodominant site on the P30 protein. Efforts have been made to know if the pentadecapeptide Trp-His-Trp-Arg-His-Arg-Ile-Pro-Leu-Gln-Leu-Ala-Ala-Gly-Arg (SEQ ID NO.48) is also recognized by the human antibodies present in the sera of a patient infected with *Toxoplasma gondii*.

The ELISA test was carried out as described in Example 2 with the following modifications: 100 μl of various dilutions of human serum of a patient infected with *Toxoplasma gondii* (positive serum—reference G8) are brought into contact with the phage clone identified, immobilized as described in Example 2, for 30 minutes at 37° C. After two washes with TBS/Tween 0.05%, 100 μl of monoclonal antibody 1E1E7 at the concentration of 6 nM are added and incubated overnight at 4° C. After four washes with TBS/ Tween, 100 μl of anti-mouse conjugate labeled with peroxidase are added and then incubated for one hour at 37° C. The enzymatic reaction for visualization was carried out by adding 100 μl of an $H_2O_2$/orthophenylenediamine (OPD) solution and incubating the sample for 30 minutes at room temperature. The staining reaction is stopped by adding 50 μl of 1.8N sulfuric acid. The optical density is measured on a BioMé rieux plate reader at 492 nm. Moreover, a control was produced, under the same reaction conditions but with a human serum not infected with *Toxoplasma gondii* (negative serum), in order to ensure that the phage clone identified reacts specifically with the human serum of a patient infected with *Toxoplasma gondii*.

Figure 2:
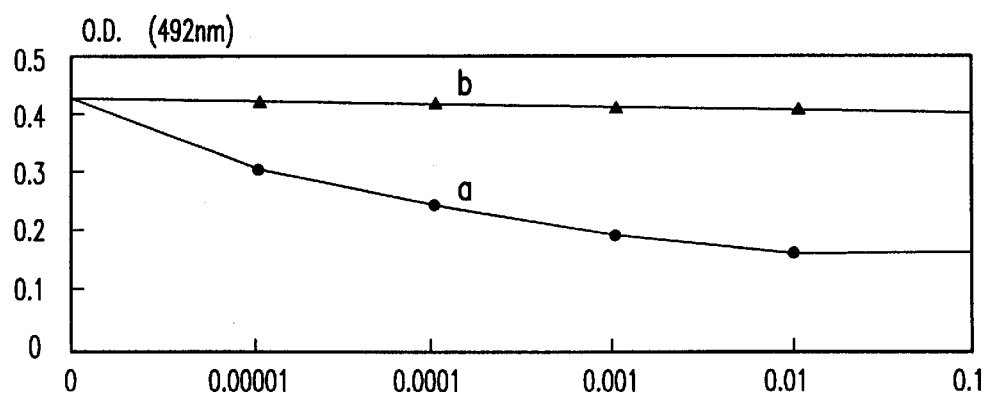
FIG. 2 illustrates, according to curve a, the inhibition, by a serum of a patient infected with *Toxoplasma gondii*, of the ELISA response obtained with the phage clone identified in Example 2, compared with an uninfected control serum, according to curve b. The dilutions of said serum are indicated on the x-axis and the optical density values measured at 492 nm on the y-axis.

The results (FIG. 2) show that when the positive human serum is diluted 1/100,000, a 27% inhibition of the attachment of the monoclonal antibody 1E1E7 is observed, and that from the 1/100 dilution of the human serum, the inhibition is maximum and is up to 60%.

This example therefore shows that the phages containing the sequence Trp-His-Trp-Arg-His-Arg-Ile-Pro-Leu-Gln-Leu-Ala-Ala-Gly-Arg (SEQ ID NO.48) are indeed recognized by the antibodies present in the sera of patients infected with *Toxoplasma gondii*.

EXAMPLE 5

Multiple syntheses of overlapping Pentadecapeptides and immunological analysis of said peptides by the ELISA technique.

Having obtained phage clones which give positive and specific responses during immunoanalysis, we tried to determine the minimum motif recognized specifically by the monoclonal antibody 1E1E7 in the sequence Trp-His-Trp-Arg-His-Arg-Ile-Pro-Leu-Gln-Leu-Ala-Ala-Gly-Arg (SEQ ID NO.48).

For that, we carried out the chemical synthesis of overlapping peptides which cover this sequence according to the technologies developed on the one hand by Berg et al. (1989, J. Ann. Chem. Soc., 111, 8024–8026) and marketed by Cambridge Research Biochemicals (tradename: Spotscan) and on the other hand by Geysen et al. (1987, J. of Immunological Methods, 102, 259–274) and marketed by Chiron (tradename: Pepscan) which are both based on the simultaneous synthesis of a large number of peptides and on their analysis by ELISA.

These methods allow the synthesis of overlapping peptides reproducing a determined sequence.

According to the "pepscan" technique, the synthesis is carried out with nonesterified amino acids, protected by an FMOC group (Nova Biochem). The activated esters of amino acids are formed directly on a "crown" during the coupling reaction. After deprotection of the amino acids by a 20% solution of piperidine in N,N-dimethylformamide (DMF), the first amino acid is coupled to the "crown" at the concentration of 30 or 60 nM. The coupling reactions use benzotriazol-1-yloxytris(dimethylamino)phosphonium hexafluorophosphate (BOP) as coupling agent, hydroxybenzotriazole (HOBT) and N,N-diisopropylethylamine (DIEA) to activate the reaction. The amino acids solubilized in N-methylpyrrolidone (NMP) are distributed into the various wells of the ELISA plate and brought into contact with the "crowns" overnight at room temperature. The peptides are synthesized by means of successive deprotection cycles with piperidine, washing with DMF and addition of one amino acid per day. After adding the last amino acid, the terminal amino group is acylated with a mixture of DMF:acetic anhydride: tri-ethylamine (5:2:1, v/v/v) and the side chain-protecting groups are removed with the aid of a mixture of tri-fluoroacetic acid:water:phenol:ethanedithiol:thioanisol (85:4:5:2:4, v:v:w:v:v). The immunoreactivity of the peptides thus coupled to the surface of the "crowns" can then be tested by ELISA.

According to the "Spotscan" technique, the synthesis of the peptides is carried out on cellulose membranes (Cambridge Research Biochemicals). The principle of the method is the same as that for Pepscan. The esterified amino acids are solubilized in N-methylpyrrolidone (NMP) at the concentration of 300 nM and 0.9 μl are deposited at the level of spots for the deposition of bromophenol blue. After a 15 minute incubation, another deposition of amino acids is carried out followed by another 15 minute incubation. If the coupling between the two amino acids is carried out correctly, a change in color is observed (passage from blue to yellowish green). After three washes in DMF, an acetylation step is carried out with acetic anhydride. Then the terminal amino groups of the peptides being synthesized are deprotected with 20% piperidine in DMF. The deposition spots are restained with a 1% bromophenol blue solution in DMF, washed three times with methanol and dried. These operations as a whole constitute a cycle for addition of an amino acid and this cycle is repeated up to the end of the synthesis. When all the amino acids have been added, the $NH_2$-terminal group of the last amino acid is deprotected with 20% piperidine in DMF and is acetylated with acetic anhydride. The side chain protecting groups are removed by a dichloromethane:trifluoroacetic acid:triisobutylsilane mixture (5 ml:5 ml:250 μl). The immunoreactivity of the peptides thus synthesized can then be tested by ELISA.

In order to reproduce the entire pentadecapeptide included in the phage clone isolated and to determine the possible role of the contiguous amino acids belonging to the sequence of the PIII protein of the phage (see Example 1), the chemical synthesis of overlapping pentadecapeptides, which cover the sequence Phe-Tyr-Ser-His-Ser-Ala-Asp-Gly-Ala-Trp-His-Trp-Arg-His-Arg-Ile-Pro-Leu-Gln -Leu-Ala-Ala-Gly-Arg-Gly-Ala-Ala-Gly-Ala-Glu-Thr-Val-Glu-Ser-Cys-Leu-Ala (SEQ ID NO.59), was carried out on an activated cellulose membrane ("Spotscan").

After synthesis of the various pentadecapeptides, the membrane is rinsed with methanol, washed in TBS (0.1M Tris, pH 7.2) and then incubated overnight at room temperature in saturation buffer (marketed by Cambridge Research Biochemicals). After several washes with TBS-T (0.1M Tris, pH 7.2-0.05% Tween 20), the membrane is brought into contact with a solution of anti-P30 monoclonal antibody 1E1E7 (60 nM) and incubated for 4 hours at room temperature. After three washes with TBS-T, the anti-mouse immunoglobulin conjugate labeled with galactosidase (marketed by Cambridge Research Biochemicals) is added at a 1/200 dilution and the whole is incubated for two hours at room temperature. After several washes of the membrane with PBS-Tween 0.05 % and PBS, the immunoreactivity at the level of the various spots is visualized by adding a solution of substrate (5-bromo-4-chloro-3-indoyl-D-galactopyranoside in PBS containing magnesium chloride and potassium ferricyanide) and incubating for 10 to 40 minutes. The color of the spots is assessed qualitatively.

Sequential analysis of the results obtained shows that a first color is obtained with the sequence Ser-Ala-Asp-Gly-Ala-Trp-His-Trp-Arg-His-Arg-Ile-Pro-Leu-Gln (SEQ ID NO.23). Then the blue color increases gradually along the sequence of the phage to reach a maximum with the sequences His-Arg-Ile-Pro-Leu-Gln-Leu-Ala-Ala-Gly-Arg-Gly-Ala-Ala-Gly (SEQ ID No.9) and Arg-Ile-Pro-Leu-Gln-Leu-Ala-Ala-Gly-Arg-Gly-Ala-Ala-Gly-Ala (SEQ ID NO.32). A very slight color is still visible for the sequence Ile-Pro-Leu-Gln-Leu-Ala-Ala-Gly-Arg-Gly-Ala-Ala-Gly-Ala-Glu (SEQ ID NO.33) but it disappears completely from the sequence Pro-Leu-Gln-Leu-Ala-Ala-Gly-Arg-Gly-Ala-Ala-Gly-Ala-Glu-Thr (SEQ ID NO.34).

These results have, moreover, been confirmed by the synthesis of the same peptides by the so-called "Pepscan" technique which, contrary to the so-called "Spotscan" technique, makes it possible to quantify the level of ELISA response obtained for each peptide.

The "crowns" carrying the pentadecapeptides, synthesized as described above in microtiter plates, are saturated for one hour with the aid of a solution con taining 1% ovalbumin, 1% bovine serum albumin in PBS-T (phosphate buffer, pH 7.2, containing 0.1% Tween 20). After incubating overnight at 4° C. with 150 μl of monoclonal antibody 1E1E7 diluted 1/100 (60 nM), and four washes with PBS-T, the wells of the plate are incubated for one hour with peroxidase-labeled anti-mouse conjugate diluted 1/1000 (marketed by Jackson Immuno Research Laboratories Inc.). Following a series of four washes with PBS-T, the wells of the plate are incubated with the ABTS substrate (0.5 mg/ml of azino-di-3-ethylbenzo-thiazoline-6-sulfonate in citrate buffer, pH 4.0, containing 0.03% hydrogen peroxide). The absorbance measurements are carried out at 405 nm on an ELISA plate reader (BioMé rieux).

Moreover, two pentadecapeptides containing the sequences Pro-Leu-Ala-Gln (SEQ ID NO.60) and Gly-Leu-Ala-Gln (SEQ ID NO.61) were synthesized as positive and negative controls, respectively, and were tested using an anti-(Pro-Leu-Ala-Gln) (SEQ ID NO.60) monoclonal antibody.

Figure 3:
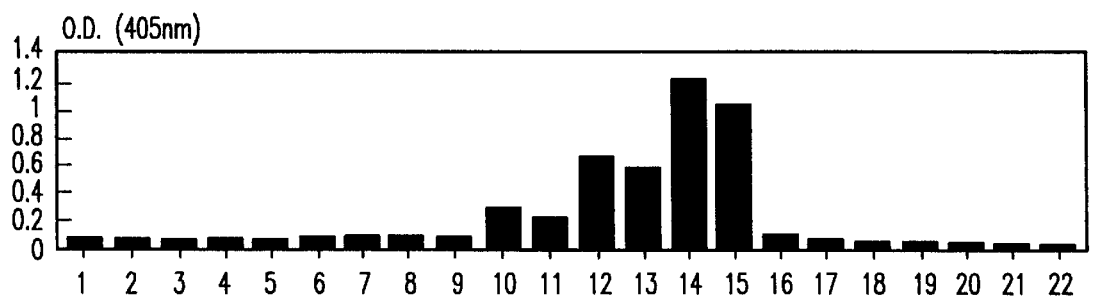
FIG. 3 is a histogram illustrating the ELISA response of the following overlapping pentadecapeptides synthesized according to the Pepscan technique:
(1) FYSHSADGAWHWRHR (SEQ ID NO.19) (12) WRHRIPLQLAAGRGA (SEQ ID NO.30)
(2) YSHSADGAWHWRHRI (SEQ ID NO.20) (13) RHRIPLQLAAGRGAA (SEQ ID NO.31)
(3) SHSADGAWHWRHRIP (SEQ ID NO.21) (14) HRIPLQLAAGRGAAG (SEQ ID NO.9)
(4) HSADGAWHWRHRIPL (SEQ ID NO.22) (15) RIPLQLAAGRGAAGA (SEQ ID NO.32)
(5) SADGAWHWRHRIPLQ (SEQ ID NO.23) (16) IPLQLAAGRGAAGAE (SEQ ID NO.33)
(6) ADGAWHWRHRIPLQL (SEQ ID NO.24) (17) PLQLAAGRGAAGAET (SEQ ID NO.34)
Figure 4A:
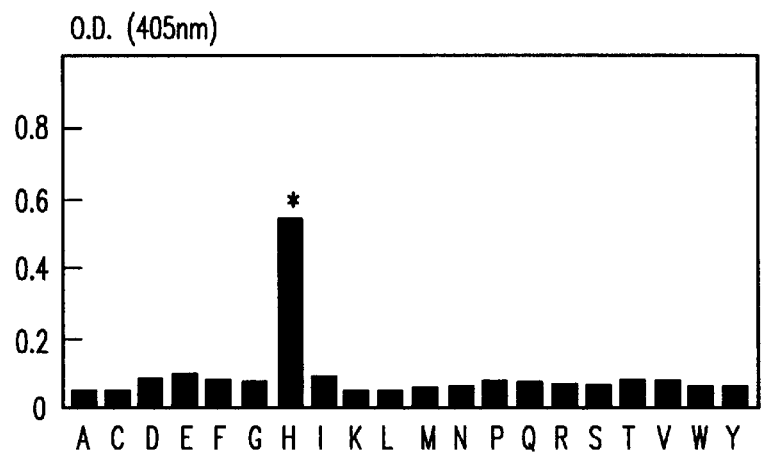
Figure 4B:
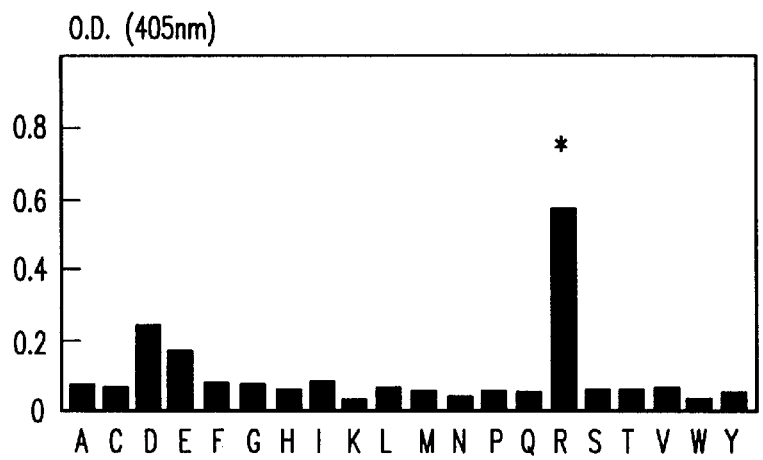
Figure 4C:
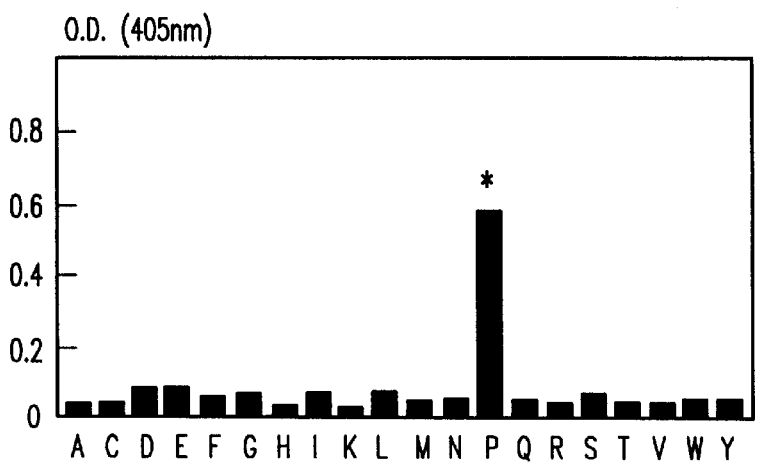
Figure 4D:
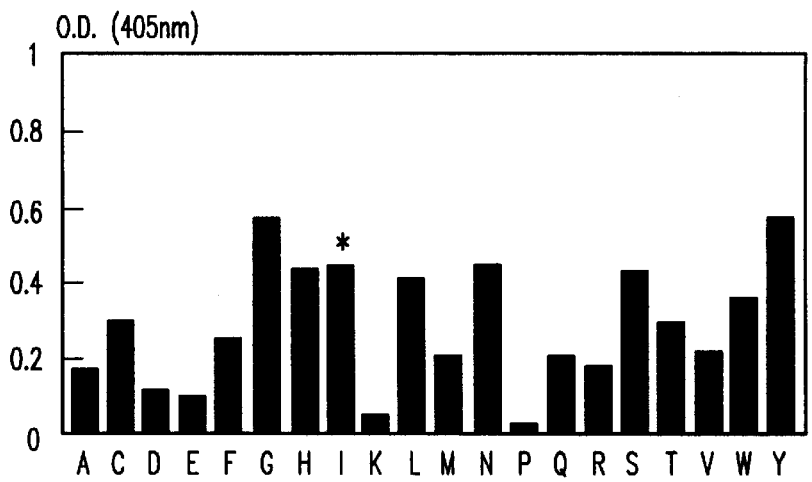
Figure 4E:
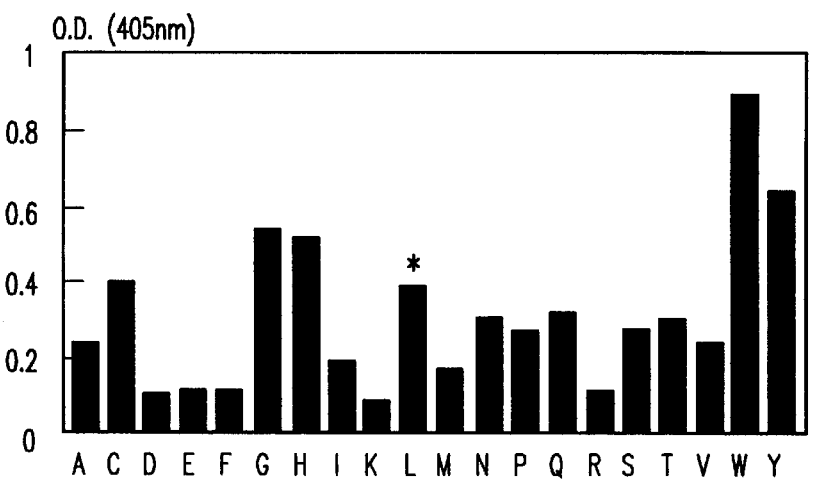
Figure 4F:
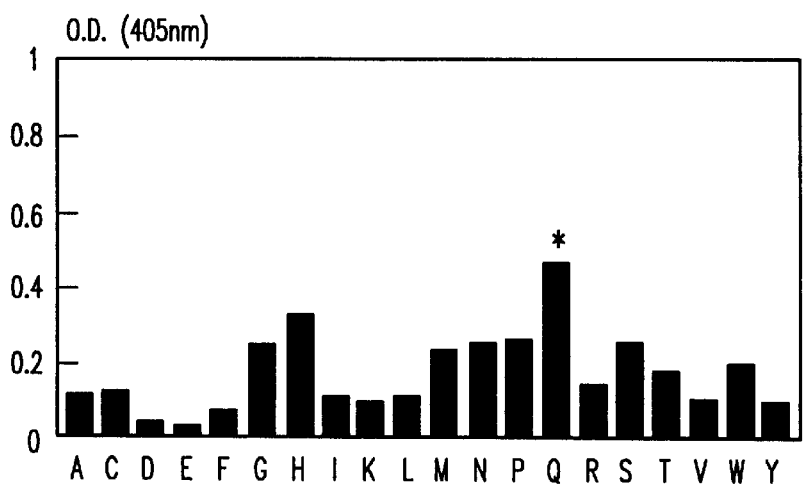

These results (FIG. 3) confirm the results obtained during the selection of the phage clone (Example 1) containing a nucleic sequence encoding the pentadecapeptide Trp-His-Trp-Arg-His-Arg-Ile-Pro-Leu-Gln-Leu-Ala-Ala-Gly-Arg (SEQ ID NO.48). Moreover, they show that the first amino acids Trp-His-Trp-Arg (SEQ ID NO.62) at the NH$_2$ end are not necessary for the recognition of the peptide by the anti-P30 monoclonal antibodies and that, on the other hand, the addition of the sequence Gly-Ala-Ala-Gly (SEQ ID NO.63) to the COOH end of the peptide makes it possible to improve this reactivity. Finally, these results show that an isolated peptide, in which a succession of 11 contiguous amino acids does not exhibit more than 36% homology with the sequence of the native P30 protein, is capable of being recognized by antibodies specific for said protein.

EXAMPLE 6

Substitutions of amino acids in the peptide His-Arg-Ile-Pro-Leu-Gln-Leu-Ala-Ala-Gly-Arg-Gly-Ala-Ala-Gly (SEQ ID NO.9) and immunological analysis of said modified peptides by the ELISA technique.

In order to determine to what extent the nature of the various amino acids constituting the peptide His-Arg-Ile-Pro-Leu-Gln-Leu-Ala-Ala-Gly-Arg-Gly-Ala-Ala-Gly (SEQ ID No.9) may vary without affecting the antigenic properties of said peptide toward anti-P30 antibodies, point substitution tests were carried out.

The peptides were synthesized according to the so-called "Pepscan" method described in the preceding example by substituting on the peptide each amino acid at a given position by the other nineteen. These peptides were then tested by the ELISA technique as described above. The importance of each residue can thus be examined and a peptide covering the best amino acids at each position can then be synthesized.

The results obtained (FIGS. 4A to 4F) show that the Histidine in position 1, the Arginine in position 2, the Proline in position 4 and the Glutamine in position 6 appear to play an important role in the recognition by the anti-P30 monoclonal antibody 1E1E7. These amino acids give the highest signals and should therefore be conserved in the final peptide.

The results obtained also show that when the Isoleucine in position 3 is replaced with:

Glycine or Tyrosine, a better response is observed,

Histidine, Leucine, Asparagine or Serine, a response is observed which is equivalent to that observed in the presence of Isoleucine, Proline, Lysine, Aspartic Acid or Glutamic Acid, a complete disappearance of the recognition by the monoclonal antibody is observed.

The results show, in addition, that when the Leucine in position 5 is replaced with:

the aromatic amino acids Tyrosine and Tryptophan, a very clear increase in the ELISA response is obtained, Glycine and Histidine, an increase in the response is also obtained with the antibodies, Cysteine, a response is observed which is equivalent to that observed in the presence of Leucine, Lysine, Arginine, Phenylalanine, Aspartic Acid and Glutamic Acid, a sharp decrease in the response is obtained.

For the other positions tested (Leucine in position 7, Alanine in position 8 and in position 9, Glycine in position 10 and Arginine in position 11), the results, which are obtained by their substitution by the other 19 amino acids, are not significantly different from those observed with the reference peptide His-Arg-Ile-Pro-Leu-Gln-Leu-Ala-Ala-Gly-Arg-Gly-Ala-Ala-Gly (SEQ ID NO.9).

EXAMPLE 7

Chemical synthesis of two pentadecapeptides and ELISA test with positive human sera.

Based on the information obtained from the preceding examples, the pentadecapeptides His-Arg-Ile-Pro-Leu-Gln-Leu-Ala-Ala-Gly-Arg-Gly-Ala-Ala-Gly (SEQ ID No.9) and His-Arg-Ile-Pro-Trp-Gln-Leu-Ala-Ala-Gly-Arg-Gly-Ala-Ala-Gly (SEQ ID No.10) were synthesized according to the method described in Patent Application No. EP 93420183.

These peptides were then tested by ELISA with respect to their reactivity toward several sera from patients infected with *Toxoplasma gondii*.

The wells of a Maxisorb (tradename, Nunc) micro-titer plate are saturated with 100 μl of a 50 mM HCO$_3$Na solution, pH 9.6, containing 10 μg/ml of peptide to be tested for 2 hours at 37° C. The plate is washed with PBS buffer/Tween 20 0.05%. The wells are then saturated with 100 μl of washing buffer supplemented with 1% bovine serum albumin for 1 hour at 37° C. and then washed as described above.

The sera to be analyzed are diluted 1/200 and 1/1000 in the saturation buffer and incubated for 2 hours at 37° C. After washing, a solution of anti-human immunoglobulin goat "antibody" conjugate labeled with peroxidase (marketed by Jackson Immuno Research Laboratories Inc.) is added at the dilution of 1/10,000 and the plates are incubated for 1 hour at 37° C. After washing, the ortho-phenylenediamine (OPD) substrate is added and the reaction is stopped after 10 minutes by the addition of 50 μl of H₂SO₄. The optical density is read at 492 nm.

The results obtained show that these two peptides do not at all react with the negative sera and that they are specifically recognized by the sera from patients infected with *Toxoplasma gondii*.

---

I claim:

1. An isolated polypeptide that binds specifically with an anti-*Toxoplasma gondii* P30 protein antibody, whose peptide sequence comprises SEQ ID No.2.

2. The polypeptide as claimed in claim 1, whose peptide sequence comprises a sequence selected from the group consisting of SEQ ID No. 3, and SEQ ID No. 4.

3. The polypeptide as claimed in claim 2, whose peptide sequence comprises a sequence selected from the group consisting of SEQ ID No. 5, and SEQ ID No. 6.

4. The polypeptide as claimed in claim 3, whose peptide sequence comprises a peptide sequence selected from the group consisting of SEQ ID No. 7, SEQ ID No. 8, SEQ ID No. 9, and SEQ ID No. 10.

5. The polypeptide as claimed in claim 1, whose peptide sequence consists of a peptide sequence selected from the group consisting of SEQ ID No. 2, SEQ ID No. 3, SEQ ID No. 4, SEQ ID No. 5, SEQ ID No. 6, SEQ ID No. 7, SEQ ID No. 8, SEQ ID No. 9, and SEQ ID No. 10.

6. An active immunotherapeutic composition, comprising as an active ingredient, a polypeptide as claimed in claim 4.

7. An active immunotherapeutic composition according to claim 6, wherein said composition is a vaccinal preparation.

8. An active immunotherapeutic composition according to claim 6, said active ingredient being conjugated with a support, wherein said support is immunologically compatible with a reagent.

9. An active immunotherapeutic composition according to claim 6, wherein said active ingredient is conjugated with a pharmaceutically acceptable excipient.

10. The polypeptide as claimed in claim 1, wherein said polypeptide consists of a peptide sequence wherein every succession of 6 contiguous amino acids exhibits at most 67% homology with SEQ ID No. 1.

11. A reagent for the detection of a *Toxoplasma gondii* infection, which comprises, as reactive substance, a polypeptide as claimed in claim 1.

12. A reagent according to claim 11, wherein said polypeptide is labeled.

13. A kit for the detection of a *Toxoplasma gondii* infection, wherein a reagent as claimed in claim 11 is supported by a solid support which is immunologically compatible with said reagent.

14. A process of the detection, separation, purification, and/or assay of anti-*Toxoplasma gondii* P30 protein antibodies in a sample of biological fluid, wherein said sample is brought into contact with a reagent as claimed in claim 11, under conditions which allow an immunological reaction, and wherein the immune complex which may be formed is detected, separated and quantified.

15. A process for assaying the *Toxoplasma gondii* P30 protein in a sample of a biological fluid, by a competition technique, wherein said sample is brought into contact simultaneously with a predetermined quantity of anti-P30 protein antibodies, and a predetermined quantity of a reagent as claimed in claim 11, and the quantity of P30 protein in said sample is determined by deduction from the measured quantity of the immune complex formed between the reagent and said anti-P30 protein antibodies.

16. A process for assaying the *Toxoplasma gondii* P30 protein in a sample of a biological fluid, wherein in a first instance, said sample is brought into contact with a predetermined quantity of anti-P30 protein antibodies, in a second instance, a predetermined quantity of a reagent as claimed in claim 11 is added and the quantity of P30 protein in said sample is determined by deduction from the measured quantity of the immune complex formed between the reagent and said anti-P30 protein antibodies.

* * * * *

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
        (A) LENGTH: 336 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:1:

```
Met Ser Val Ser Leu His His Phe Ile Ile Ser Ser Gly Phe Leu Thr
 1               5                  10                  15
Ser Met Phe Pro Lys Ala Val Arg Arg Ala Val Thr Ala Gly Val Phe
                20                  25                  30
Ala Ala Pro Thr Leu Met Ser Phe Leu Arg Cys Gly Val Met Ala Ser
            35                  40                  45
Asp Pro Pro Leu Val Ala Asn Gln Val Val Thr Cys Pro Asp Lys Lys
        50                  55                  60
Ser Thr Ala Ala Val Ile Leu Thr Pro Thr Glu Asn His Phe Thr Leu
65                  70                  75                  80
Lys Cys Pro Lys Thr Ala Leu Thr Glu Pro Pro Thr Leu Ala Tyr Ser
                85                  90                  95
Pro Asn Arg Gln Ile Cys Pro Ala Gly Thr Thr Ser Ser Cys Thr Ser
            100                 105                 110
Lys Ala Val Thr Leu Ser Ser Leu Ile Pro Glu Ala Glu Asp Ser Trp
        115                 120                 125
Trp Thr Gly Asp Ser Ala Ser Leu Asp Thr Ala Gly Ile Lys Leu Thr
    130                 135                 140
Val Pro Ile Glu Lys Phe Pro Val Thr Thr Gln Thr Phe Val Val Gly
145                 150                 155                 160
Cys Ile Lys Gly Asp Asp Ala Gln Ser Cys Met Val Thr Val Thr Val
                165                 170                 175
Gln Ala Arg Ala Ser Ser Val Val Asn Val Ala Arg Cys Ser Tyr
            180                 185                 190
Gly Ala Asp Ser Thr Leu Gly Pro Val Lys Leu Ser Ala Glu Gly Pro
        195                 200                 205
Thr Thr Met Thr Leu Val Cys Gly Lys Asp Gly Val Lys Val Pro Gln
    210                 215                 220
Asp Asn Asn Gln Tyr Cys Ser Gly Thr Thr Leu Thr Gly Cys Asn Glu
225                 230                 235                 240
Lys Ser Phe Lys Asp Ile Leu Pro Lys Leu Thr Glu Asn Pro Trp Gln
                245                 250                 255
Gly Asn Ala Ser Ser Asp Lys Gly Ala Thr Leu Thr Ile Asn Lys Glu
            260                 265                 270
Ala Phe Pro Ala Glu Ser Lys Ser Val Ile Ile Gly Cys Thr Gly Gly
        275                 280                 285
```

```
Ser  Pro  Glu  Lys  His  His  Cys  Thr  Val  Lys  Leu  Glu  Phe  Ala  Gly  Ala
     290                 295                 300

Ala  Gly  Ser  Ala  Lys  Ser  Ser  Ala  Gly  Thr  Ala  Ser  His  Val  Ser  Ile
305                      310                 315                          320

Phe  Ala  Met  Val  Thr  Gly  Leu  Ile  Gly  Ser  Ile  Ala  Ala  Cys  Val  Ala
                    325                 330                      335
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Region
        ( B ) LOCATION: 3
        ( D ) OTHER INFORMATION: /note= "Xaa is Gly or His or Leu or
            Asn or Ser or Tyr or Ile"

( i x ) FEATURE:
        ( A ) NAME/KEY: Region
        ( B ) LOCATION: 5
        ( D ) OTHER INFORMATION: /note= "Xaa is Leu or Trp or Cys or
            Gly or His or Tyr"

( x i ) SEQUENCE DESCRIPTION: SEQ ID NO:2:

```
His  Arg  Xaa  Pro  Xaa  Gln
 1                    5
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Region
        ( B ) LOCATION: 3
        ( D ) OTHER INFORMATION: /note= "Xaa is Gly or His or Leu or
            Asn or Ser or Tyr or Ile"

( i x ) FEATURE:
        ( A ) NAME/KEY: Region
        ( B ) LOCATION: 5
        ( D ) OTHER INFORMATION: /note= "Xaa is Leu or Trp or Cys or
            Gly or His or Tyr"

( i x ) FEATURE:
        ( A ) NAME/KEY: Region
        ( B ) LOCATION: 7..11
        ( D ) OTHER INFORMATION: /note= "Xaa is an amino acid
            selected from the group consisting of the 20 amino
            acids, each Xaa being independently selected from the
            other locations."

( x i ) SEQUENCE DESCRIPTION: SEQ ID NO:3:

```
His  Arg  Xaa  Pro  Xaa  Gln  Xaa  Xaa  Xaa  Xaa  Xaa
 1                    5                      10
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: Not Relevant (D) TOPOLOGY: linear (ii) MOLECULE TYPE: peptide (ix) FEATURE:
    (A) NAME/KEY: Region
    (B) LOCATION: 3
    (D) OTHER INFORMATION: /note= "Xaa is Gly or His or Leu or Asn or Ser or Tyr or Ile"

(ix) FEATURE:
    (A) NAME/KEY: Region
    (B) LOCATION: 5
    (D) OTHER INFORMATION: /note= "Xaa is Leu or Trp or Cys or Gly or His or Tyr"

(ix) FEATURE:
    (A) NAME/KEY: Region
    (B) LOCATION: 7..11
    (D) OTHER INFORMATION: /note= "Xaa is an amino acid selected from the group consisting of the 20 amino acids, each Xaa being independently selected from the other locations."

(xi) SEQUENCE DESCRIPTION: SEQ ID NO:4:

```
His Arg Xaa Pro Xaa Gln Xaa Xaa Xaa Xaa Xaa Gly Ala Ala Gly
 1               5                  10                  15
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Region
        (B) LOCATION: 3
        (D) OTHER INFORMATION: /note= "Xaa is Gly or His or Leu or Asn or Ser or Tyr or Ile"

(ix) FEATURE:
        (A) NAME/KEY: Region
        (B) LOCATION: 5
        (D) OTHER INFORMATION: /note= "Xaa is Leu or Trp or Cys or Gly or His or Tyr"

(xi) SEQUENCE DESCRIPTION: SEQ ID NO:5:

```
His Arg Xaa Pro Xaa Gln Leu Ala Ala Gly Arg
 1               5                  10
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Region
        (B) LOCATION: 3
        (D) OTHER INFORMATION: /note= "Xaa is Gly or His or Leu or Asn or Ser or Tyr or Ile"

(ix) FEATURE:
        (A) NAME/KEY: Region
        (B) LOCATION: 5
        (D) OTHER INFORMATION: /note= "Xaa is Leu or Trp or Cys or Gly or His or Tyr"

( x i ) SEQUENCE DESCRIPTION: SEQ ID NO:6:

His Arg Xaa Pro Xaa Gln Leu Ala Ala Gly Arg Gly Ala Ala Gly
1               5                   10                  15

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:7:

His Arg Ile Pro Leu Gln Leu Ala Ala Gly Arg
1               5                   10

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:8:

His Arg Ile Pro Trp Gln Leu Ala Ala Gly Arg
1               5                   10

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:9:

His Arg Ile Pro Leu Gln Leu Ala Ala Gly Arg Gly Ala Ala Gly
1               5                   10                  15

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:10:

His Arg Ile Pro Trp Gln Leu Ala Ala Gly Arg Gly Ala Ala Gly
1               5                   10                  15

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other DNA ( i x ) FEATURE:
    ( A ) NAME/KEY: misc_feature
    ( B ) LOCATION: 6, 33
    ( D ) OTHER INFORMATION: /note= "N is A, G, C or T if M is C
        in codon MGN, or N is R if M is A in codon MGN"

( i x ) FEATURE:
    ( A ) NAME/KEY: misc_feature
    ( B ) LOCATION: 15, 21
    ( D ) OTHER INFORMATION: /note= "N is R if Y is T in codon
        YTN, or N is A, G, C or T if Y is C in codon YTN"

( x i ) SEQUENCE DESCRIPTION: SEQ ID NO:11:

```
CAY  MGN  ATH  CCN  YTN  CAR  YTN  GCN  GCN  G-
GN   MGN                                        33
His  Arg  Ile  Pro  Leu  Gln  Leu  Ala  Ala  Arg
 1              5                        10
```

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other DNA ( i x ) FEATURE:
        ( A ) NAME/KEY: misc_feature
        ( B ) LOCATION: 6, 33
        ( D ) OTHER INFORMATION: /note= "N is A, G, C or T if M is C
            in codon MGN, or N is R if M is A in codon MGN"

( i x ) FEATURE:
        ( A ) NAME/KEY: misc_feature
        ( B ) LOCATION: 21
        ( D ) OTHER INFORMATION: /note= "N is R if Y is T in codon
            YTN, or N is A, G, C or T if Y is C in codon YTN"

( x i ) SEQUENCE DESCRIPTION: SEQ ID NO:12:

```
CAY  MGN  ATH  CCN  TGG  CAR  YTN  GCN  GCN  GGN  MGN      33
His  Arg  Ile  Pro  Trp  Gln  Leu  Ala  Ala  Ala  Arg
 1              5                        10
```

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other DNA ( i x ) FEATURE:
        ( A ) NAME/KEY: misc_feature
        ( B ) LOCATION: 6, 33
        ( D ) OTHER INFORMATION: /note= "N is A, G, C or T if M is C
            in codon MGN, or N is R if M is A in codon MGN"

( i x ) FEATURE:
        ( A ) NAME/KEY: misc_feature
        ( B ) LOCATION: 15, 21
        ( D ) OTHER INFORMATION: /note= "N is R if Y is T in codon
            YTN, or N is A, G, C or T if Y is C in codon YTN"

( x i ) SEQUENCE DESCRIPTION: SEQ ID NO:13:

```
CAY  MGN  ATH  CCN  YTN  CAR  YTN  GCN  GCN  G-
GN   MGN  GGN  GCN  GCN  GGN                    45
His  Arg  Ile  Pro  Leu  Gln  Leu  Ala  Ala  Ala  Arg  Gly  Ala  Ala  Gly
 1              5                        10                         15
```

( 2 ) INFORMATION FOR SEQ ID NO:14:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other DNA (ix) FEATURE:
(A) NAME/KEY: misc_feature
(B) LOCATION: 6, 33
(D) OTHER INFORMATION: /note= "N is A, G, C or T if M is C in codon MGN, or N is R if M is A in codon MGN"

(ix) FEATURE:
(A) NAME/KEY: misc_feature
(B) LOCATION: 21
(D) OTHER INFORMATION: /note= "N is R if Y is T in codon YTN, or N is A, G, C or T if Y is C in codon YTN"

(xi) SEQUENCE DESCRIPTION: SEQ ID NO:14:

```
CAY  MGN  ATH  CCN  TGG  CAR  YTN  GCN  GCN  GGN  MGN  GGN  GCN  GCN  GGN      45
His  Arg  Ile  Pro  Trp  Gln  Leu  Ala  Ala  Ala  Arg  Gly  Ala  Ala  Gly
```

(2) INFORMATION FOR SEQ ID NO:15:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:15:

```
Gly  Glu  Thr  Gly  Gly  Arg  Ser  Arg  Ser  Ser  Trp  Asn  Ala  Arg  Leu  Ala
 1              5                        10                           15

Arg  Thr  Gly  Arg  Asn  Phe  Arg  Phe  Tyr  Asp  Pro  Ala  Lys  Val  Lys  Ser
              20                        25                      30

Leu  Val  Val  Thr  Asp  Phe  Ser  Arg  Leu  Met  Leu  Arg  Lys  Ala  Leu  Glu
              35                        40                      45

Lys  Lys  Glu  Ala  Leu  Arg
              50
```

(2) INFORMATION FOR SEQ ID NO:16:

(i) SEQUENCE CHARACTERISTICS:
(A) LENGTH: 19 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:16:

```
Thr  Asp  Phe  Ser  Arg  Leu  Met  Leu  Arg  Lys  Ala  Leu  Glu  Lys  Lys  Glu
 1              5                        10                           15

Ala  Leu  Arg
```

(2) INFORMATION FOR SEQ ID NO:17:

(i) SEQUENCE CHARACTERISTICS:
(A) LENGTH: 19 amino acids
(B) TYPE: amino acid
(C) STRANDEDNESS: Not Relevant
(D) TOPOLOGY: linear (ii) MOLECULE TYPE: peptide ( x i ) SEQUENCE DESCRIPTION: SEQ ID NO:17:

Xaa Asp Phe Ser Arg Leu Met Leu Arg Lys Ala Leu Glu Lys Lys Glu
1               5                   10                  15

Ala Leu Arg ( 2 ) INFORMATION FOR SEQ ID NO:18:

( i ) SEQUENCE CHARACTERISTICS:
    ( A ) LENGTH: 85 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:18:

Glu Gly Glu Thr Gly Gly Arg Ser Arg Ser Ser Trp Asn Ala Arg Leu
1               5                   10                  15

Ala Arg Lys Gln Ala Ile Asp Asp Gly Gln Gln Glu Glu Arg Gly Gln
                20                  25                  30

Leu Leu Gln Cys Arg Ser Ile Gly Ile Arg Pro Ala Gly Ser Leu Glu
            35                  40                  45

Ser Arg Arg Gly Ser Gln Glu Ser Gly Leu Arg Ala Ser Val Gly Phe
        50                  55                  60

Asp Ser Arg Val Leu Arg Cys Arg Lys Gly Gln Leu Arg Val Gly Glu
65                  70                  75                  80

Phe Arg Arg Pro Ala
                85

( 2 ) INFORMATION FOR SEQ ID NO:19:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:19:

Phe Tyr Ser His Ser Ala Asp Gly Ala Trp His Trp Arg His Arg
1               5                   10                  15

( 2 ) INFORMATION FOR SEQ ID NO:20:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:20:

Tyr Ser His Ser Ala Asp Gly Ala Trp His Trp Arg His Arg Ile
1               5                   10                  15

( 2 ) INFORMATION FOR SEQ ID NO:21:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:21:

Ser His Ser Ala Asp Gly Ala Trp His Trp Arg His Arg Ile Pro
1               5                   10                  15

( 2 ) INFORMATION FOR SEQ ID NO:22:

( i ) SEQUENCE CHARACTERISTICS:
      ( A ) LENGTH: 15 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:22:

His Ser Ala Asp Gly Ala Trp His Trp Arg His Arg Ile Pro Leu
1               5                   10                  15

( 2 ) INFORMATION FOR SEQ ID NO:23:

( i ) SEQUENCE CHARACTERISTICS:
      ( A ) LENGTH: 15 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:23:

Ser Ala Asp Gly Ala Trp His Trp Arg His Arg Ile Pro Leu Gln
1               5                   10                  15

( 2 ) INFORMATION FOR SEQ ID NO:24:

( i ) SEQUENCE CHARACTERISTICS:
      ( A ) LENGTH: 15 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:24:

Ala Asp Gly Ala Trp His Trp Arg His Arg Ile Pro Leu Gln Leu
1               5                   10                  15

( 2 ) INFORMATION FOR SEQ ID NO:25:

( i ) SEQUENCE CHARACTERISTICS:
      ( A ) LENGTH: 15 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:25:

Asp Gly Ala Trp His Trp Arg His Arg Ile Pro Leu Gln Leu Ala
1               5                   10                  15

( 2 ) INFORMATION FOR SEQ ID NO:26:

( i ) SEQUENCE CHARACTERISTICS:
      ( A ) LENGTH: 15 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:26:

```
Gly  Ala  Trp  His  Trp  Arg  His  Arg  Ile  Pro  Leu  Gln  Leu  Ala  Ala
1                 5                          10                            15
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:27:

```
Ala  Trp  His  Trp  Arg  His  Arg  Ile  Pro  Leu  Gln  Leu  Ala  Ala  Gly
1                 5                          10                            15
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:28:

```
Trp  His  Trp  Arg  His  Arg  Ile  Pro  Leu  Gln  Leu  Ala  Ala  Gly  Arg
1                 5                          10                            15
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:29:

```
His  Trp  Arg  His  Arg  Ile  Pro  Leu  Gln  Leu  Ala  Ala  Gly  Arg  Gly
1                 5                          10                            15
```

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:30:

```
Trp  Arg  His  Arg  Ile  Pro  Leu  Gln  Leu  Ala  Ala  Gly  Arg  Gly  Ala
1                 5                          10                            15
```

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:31:

Arg His Arg Ile Pro Leu Gln Leu Ala Ala Gly Arg Gly Ala Ala
1               5                   10                  15

( 2 ) INFORMATION FOR SEQ ID NO:32:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:32:

Arg Ile Pro Leu Gln Leu Ala Ala Gly Arg Gly Ala Ala Gly Ala
1               5                   10                  15

( 2 ) INFORMATION FOR SEQ ID NO:33:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:33:

Ile Pro Leu Gln Leu Ala Ala Gly Arg Gly Ala Ala Gly Ala Glu
1               5                   10                  15

( 2 ) INFORMATION FOR SEQ ID NO:34:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:34:

Pro Leu Gln Leu Ala Ala Gly Arg Gly Ala Ala Gly Ala Glu Thr
1               5                   10                  15

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:35:

Leu Gln Leu Ala Ala Gly Arg Gly Ala Ala Gly Ala Glu Thr Val
1               5                   10                  15

( 2 ) INFORMATION FOR SEQ ID NO:36:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:36:

Gln Leu Ala Ala Gly Arg Gly Ala Ala Gly Ala Glu Thr Val Glu
1               5                   10                  15

( 2 ) INFORMATION FOR SEQ ID NO:37:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:37:

Leu Ala Ala Gly Arg Gly Ala Ala Gly Ala Glu Thr Val Glu Ser
1               5                   10                  15

( 2 ) INFORMATION FOR SEQ ID NO:38:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:38:

Ala Ala Gly Arg Gly Ala Ala Gly Ala Glu Thr Val Glu Ser Cys
1               5                   10                  15

( 2 ) INFORMATION FOR SEQ ID NO:39:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:39:

Ala Gly Arg Gly Ala Ala Gly Ala Glu Thr Val Glu Ser Cys Leu
1               5                   10                  15

( 2 ) INFORMATION FOR SEQ ID NO:40:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:40:

Xaa Arg Ile Pro Leu Gln Leu Ala Ala Gly Arg Gly Ala Ala Gly
1               5                   10                  15

( 2 ) INFORMATION FOR SEQ ID NO:41:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:41:

His Xaa Ile Pro Leu Gln Leu Ala Ala Gly Arg Gly Ala Ala Gly
1               5                   10                  15

( 2 ) INFORMATION FOR SEQ ID NO:42:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:42:

His Arg Ile Xaa Leu Gln Leu Ala Ala Gly Arg Gly Ala Ala Gly
1               5                   10                  15

( 2 ) INFORMATION FOR SEQ ID NO:43:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

His Arg Xaa Pro Leu Gln Leu Ala Ala Gly Arg Gly Ala Ala Gly
1               5                   10                  15

( 2 ) INFORMATION FOR SEQ ID NO:44:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

His Arg Ile Pro Leu Gln Xaa Ala Ala Gly Arg Gly Ala Ala Gly
1               5                   10                  15

( 2 ) INFORMATION FOR SEQ ID NO:45:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:45:

His Arg Ile Pro Leu Xaa Leu Ala Ala Gly Arg Gly Ala Ala Gly
1               5                   10                  15

( 2 ) INFORMATION FOR SEQ ID NO:46:

( i ) SEQUENCE CHARACTERISTICS:
        ( A ) LENGTH: 28 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
    ( A ) NAME/KEY: Region
    ( B ) LOCATION: 5..19
    ( D ) OTHER INFORMATION: /note= "Each Xaa is an amino acid selected independently pentadecapeptide"

( x i ) SEQUENCE DESCRIPTION: SEQ ID NO:46:

```
Ala  Asp  Gly  Ala  Xaa  Xaa  Xaa  Xaa  Xaa  Xaa  Xaa  Xaa  Xaa  Xaa  Xaa  Xaa
 1              5                             10                            15

Xaa  Xaa  Xaa  Gly  Ala  Ala  Gly  Ala  Glu  Thr  Val  Glu
                20                       25
```

( 2 ) INFORMATION FOR SEQ ID NO:47:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other DNA ( x i ) SEQUENCE DESCRIPTION: SEQ ID NO:47:

TGAATTTTCT GTATGAGG                                       18

( 2 ) INFORMATION FOR SEQ ID NO:48:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:48:

```
Trp  His  Trp  Arg  His  Arg  Ile  Pro  Leu  Gln  Leu  Ala  Ala  Gly  Arg
 1              5                        10                            15
```

( 2 ) INFORMATION FOR SEQ ID NO:49:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:49:

```
Arg  His  Trp  Arg  His  Arg  Lys  Pro  Leu  Gln  Leu  Ala  Thr  Gly  Arg
 1              5                        10                            15
```

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:50:

```
Leu  Ala  Phe  His  Arg  Phe  Asn  Leu  Ser  Arg  Pro  Leu  Gln  Arg  Asp
 1              5                        10                            15
```

( 2 ) INFORMATION FOR SEQ ID NO:51:

( i ) SEQUENCE CHARACTERISTICS:
  ( A ) LENGTH: 15 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:51:

Thr His Ser His Gln Trp Arg His His Gln Phe Pro Ala Pro Thr
1      5       10       15

( 2 ) INFORMATION FOR SEQ ID NO:52:

( i ) SEQUENCE CHARACTERISTICS:
  ( A ) LENGTH: 15 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:52:

Arg Arg Trp Val Arg Tyr Pro Val His Leu His Ser Pro Ile Val
1      5       10       15

( 2 ) INFORMATION FOR SEQ ID NO:53:

( i ) SEQUENCE CHARACTERISTICS:
  ( A ) LENGTH: 15 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:53:

Ala Arg Phe Pro Lys Glu Leu Arg Gly Ser Val Arg Ser Ala His
1      5       10       15

( 2 ) INFORMATION FOR SEQ ID NO:54:

( i ) SEQUENCE CHARACTERISTICS:
  ( A ) LENGTH: 15 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:54:

Gly Ser Trp Val Leu Arg His Ser Ser Val Gly Phe His Phe Val
1      5       10       15

( 2 ) INFORMATION FOR SEQ ID NO:55:

( i ) SEQUENCE CHARACTERISTICS:
  ( A ) LENGTH: 15 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:55:

Gly Ser Phe His Trp Phe Arg Gly Ser Arg His Val Val Val His
1      5       10       15

( 2 ) INFORMATION FOR SEQ ID NO:56:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:56:

Ser Trp Arg Phe Phe His Ser Gly Met Pro Arg Val Ser Arg Ser
1               5                   10                  15

( 2 ) INFORMATION FOR SEQ ID NO:57:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:57:

Gly Ser Pro His Arg Tyr Arg Gly Ala Arg His Val Ala Val Asp
1               5                   10                  15

( 2 ) INFORMATION FOR SEQ ID NO:58:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:58:

Trp Lys Ala Leu Phe Ser His Ser Tyr Arg Ser Ser Gly Val Pro
1               5                   10                  15

( 2 ) INFORMATION FOR SEQ ID NO:59:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:59:

Phe Tyr Ser His Ser Ala Asp Gly Ala Trp His Trp Arg His Arg Ile
1               5                   10                  15

Pro Leu Gln Leu Ala Ala Gly Arg Gly Ala Ala Gly Ala Glu Thr Val
                20                  25                  30

Glu Ser Cys Leu Ala
            35

( 2 ) INFORMATION FOR SEQ ID NO:60:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:60:

-continued

```
          Pro  Leu  Ala  Gln
          1
```

(2) INFORMATION FOR SEQ ID NO:61:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
          Gly  Leu  Ala  Gln
          1
```

(2) INFORMATION FOR SEQ ID NO:62:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

```
          Trp  His  Trp  Arg
          1
```

(2) INFORMATION FOR SEQ ID NO:63:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

```
          Gly  Ala  Ala  Gly
          1
```